(12) United States Patent
Shafer et al.

(10) Patent No.: US 6,303,835 B1
(45) Date of Patent: Oct. 16, 2001

(54) METHOD FOR RECOVERING MATERIAL VALUES FROM BISPHENOL TARS

(75) Inventors: Sheldon Jay Shafer, Clifton Park; Eric James Pressman, East Greenbush; Julia Lam Lee, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/659,460

(22) Filed: Sep. 11, 2000

(51) Int. Cl.⁷ .................................................. C07C 37/00
(52) U.S. Cl. ......................... 568/806; 568/727; 568/728
(58) Field of Search ................................... 568/806, 727, 568/728

(56) References Cited

U.S. PATENT DOCUMENTS

| | | |
|---|---|---|
| 4,131,749 | 12/1978 | Kiedik et al. . |
| 4,277,628 | 7/1981 | Carnahan . |
| 4,351,966 | 9/1982 | Flock . |
| 4,594,459 * | 6/1986 | Inoue .................................. 568/806 |

* cited by examiner

*Primary Examiner*—Michael L. Shippen
(74) *Attorney, Agent, or Firm*—Andrew C. Caruso; Noreen C. Johnson

(57) ABSTRACT

Phenol and isopropenylphenol are recovered from BPA tars by sparging the fluidized BPA tar while heating in the presence of a basic catalyst. Sparging dramatically increases the efficiency of phenol and isopropenylphenol recovery. Recovered isopropenylphenol may be converted to bisphenol A in the distillate by reaction with phenol and an acidic catalyst.

24 Claims, No Drawings

METHOD FOR RECOVERING MATERIAL VALUES FROM BISPHENOL TARS

BACKGROUND OF THE INVENTION

This invention relates to the processing of bisphenol tars which are formed as by-products when phenols are reacted with ketones under acidic conditions, and more particularly to the recovery of useful chemical values from therefrom.

Among bisphenols prepared by the reaction of phenols with ketones under acidic conditions, bisphenol A is predominant in terms of the scale of its manufacture, its relatively low cost and the multitude of suitable applications for its use. The manufacture of bisphenol A (BPA) from acetone and phenol is practiced on a large scale with hundreds of millions of pounds of BPA produced annually. Although current processes used for its manufacture represent the fruits of years of research efforts and are highly efficient a small percentage of the starting materials are lost as a tarry by-product referred to as BPA tar. Given the scale of BPA manufacture the formation of even a small percentage of BPA tar by-product is significant and amounts to millions of pounds of tar produced annually. The tars are composed of a complex mixture of compounds which renders the separation and purification of individual components costly and inefficient. Currently employed recycle strategies for recovery of material values from BPA tars have focused on tar "cracking" in which the BPA tar is heated in the presence of an acidic or basic catalyst at atmospheric pressure. The combined action of the heat and catalyst results in bond cleavage of BPA tar components resulting in generation of phenol. The liberated phenol is distilled from the reaction vessel. The recovered phenol is then further purified and recycled into applications requiring the use of phenol.

In some instances the BPA tar has been heated in the presence of a catalyst under vacuum to afford a mixture of phenol and isopropenylphenol in the distillate. Isopropenylphenol is a valuable synthetic intermediate and its recovery from BPA tar represents an attractive means for its preparation. The recovery of both phenol and isopropenylphenol when BPA tar cracking is carried out under vacuum stands in sharp contrast to BPA tar cracking at atmospheric pressure in which little or no isopropenylphenol is obtained in the distillate. The requirement that vacuum conditions be employed for the cracking of BPA tar in order to produce a distillate containing isopropenylphenol reflects the chemical instability of isopropenylphenol and is a condition which adds cost and limits the economic viability of recovering phenol-isopropenylphenol mixtures from BPA tar.

It is of interest, therefore, to develop methods for the recovery of material values from BPA tar which do not require the use of vacuum equipment but which furnish phenol-isopropenylphenol mixtures from BPA tar under atmospheric pressure, and which will be applicable to the recovery of material values from bisphenol tars other than BPA tar.

BRIEF SUMMARY OF THE INVENTION

The present invention is directed to methods for the recovery of material values from BPA tar and other bisphenol tars under conditions of atmospheric pressure and focuses on the recovery of phenol-isopropenylphenol mixtures which may be transformed into other valuable products. Because BPA tar represents the most significant bisphenol tar produced worldwide and because the chemical behavior of other bisphenol tars is analogous to the behavior BPA tar, the present invention describes the recovery of material values from BPA tar as a preferred embodiment of the invention. It should be noted that the method of the invention extends to bisphenol tars generally, and is not limited to BPA tar alone. One aspect of the invention, therefore, is a method for the recovery of material values from bisphenol tars comprising the following steps:

a. contacting the bisphenol tar with a basic catalyst in an amount in the range between about 10 and about 10,000 parts catalyst per million parts bisphenol tar, b. heating the bisphenol tar catalyst mixture at a temperature in the range between about 180° C. and about 300° C. while sparging the bisphenol tar catalyst mixture with an inert gas, and c. collecting the distillate from said bisphenol tar catalyst mixture.

Still another aspect of the present invention is the conversion of the phenol-isopropenylphenol mixture to a phenol bisphenol A mixture by effecting reaction of the isopropenylphenol, contained in the collected phenol-isopropenylphenol mixture, with phenol in the presence of an acidic catalyst.

DETAILED DESCRIPTION OF THE INVENTION

The present invention may be understood more readily by reference to the following description of preferred embodiments of the invention and the Examples included therein. In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that description includes instances where the event or circumstance occurs and instances where it does not.

"BPA" is herein defined as bisphenol A or 2,2-bis(4-hydroxyphenyl)propane or 4,4'-isopropylidenediphenol.

"p,p-BPA" is herein defined as bisphenol A or 2,2-bis(4-hydroxyphenyl)propane or 4,4'-isopropylidenediphenol.

"o,p-BPA" is herein defined as bisphenol A or 2-(2-hydroxyphenyl)-2-(4-hydroxyphenyl)propane or 2,4'-isopropylidenediphenol.

"IPP" is herein defined as isopropenyiphenol or p-isopropenylphenol or 4-(propen-2-yl)phenol.

"IPP linear dimer 1" refers to a BPA tar component having structure I.

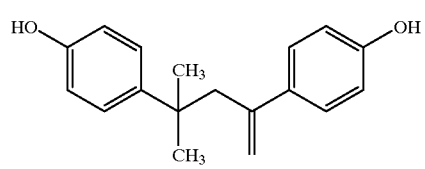

"IPP linear dimer 2" refers to a BPA tar component having structure II.

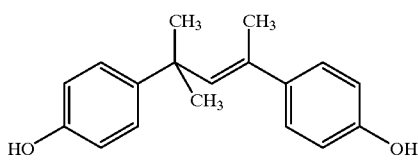

"IPP cyclic dimer 1" refers to a BPA tar component having structure III.

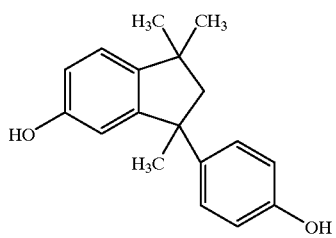

"IPP cyclic dimer 2" refers to a BPA tar component having structure IV.

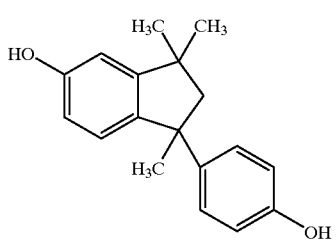

"Chroman 1" refers to a BPA tar component having structure V.

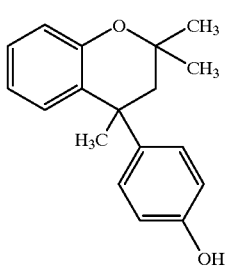

"Chroman 2" refers to a BPA tar component having structure VI.

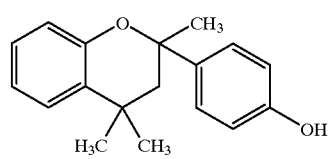

"DMX" refers to a BPA tar component having structure VII.

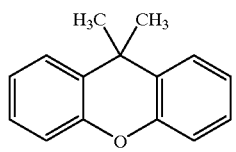

"BPX" refers to a BPA tar component having structure VIII.

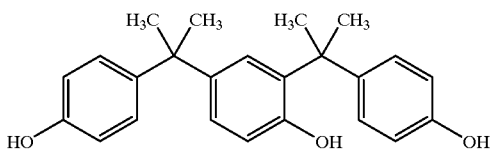

"Inert gas" is herein defined as a gas which is not reactive under the conditions used to convert BPA tar to mixtures comprising phenol and EPP and is exemplified by nitrogen, argon and steam.

"Material value" as used herein refers to the value inherent in a chemical derived from a given bisphenol tar, such as phenol at a given state of purity. The material value of phenol contained in the distillate obtained from heat treatment of BPA tar in the presence of a catalyst using the method of the present invention may at times be increased by its further purification. The material value of IPP is a result of its versatility as a chemical intermediate. IPP is a known intermediate in the preparation of the IPP linear and cyclic dimers, I–IV, and is a putative intermediate in the formation of BPA from acetone and phenol. If desired, the IPP can be reacted directly with phenol in the distillate in the presence of an added acidic catalyst to afford BPA.

The term "sparging" as used herein refers to the passage of a gas through a liquid which occurs when a gas is forced through the liquid.

"BPA tar" as used herein is defined as a by-product mixture produced during the manufacture of BPA from phenol and acetone. BPA tar varies in its composition but typically comprises the following constituents: BPA, o,p-BPA, phenol, IPP, IPP linear dimer 1, IPP linear dimer 2, IPP cyclic dimer 1, IPP cyclic dimer 2, chroman, DMX, and further condensation products of BPA with acetone or IPP such as BPX. Additionally, BPA tar includes materials of unknown structure. BPA and o,p-BPA are frequently among the chief components of the BPA tar and these two components represent most of the latent phenol and IPP contained within the BPA tar.

"Bisphenol tar" as used herein is defined as a by-product mixture produced during the manufacture of a bisphenol from a phenol and a ketone. "BPA tar" represents a particular bisphenol tar formed as a by-product when acetone and phenol are reacted together to give bisphenol A. Other bisphenol tars are produced as by-products during the manufacture of bisphenols other than BPA. These generally contain chemical components which are analogous to those found in BPA tar. Bisphenol tars are produced as by-products during the preparation of a variety of bisphenols, for example; 2,2-bis(4-hydroxy-3-methylphenyl)propane from the reaction of o-cresol with acetone; 2,2-bis(3,5-dimethyl-4-hydroxyphenyl)propane from the reaction of 2,6-xylenol with acetone; 1,1-bis(4-hydroxyphenyl)cyclohexane from the reaction of phenol with cyclohexanone; 1,1-bis(4-hydroxyphenyl)-3,3,5-trimethylcyclohexane from the reaction of phenol with 3,3,5-trimethylcyclohexanone; 1,1-bis(4-hydroxy-3-methylphenyl)cyclohexane from the reaction of o-cresol with cyclohexanone; 2,2-bis(4-hydroxyphenyl)butane from the reaction of phenol with 2-butanone. The term "bisphenol tar" as used herein further includes by-products formed during the manufacture of trisphenols such as THPE (1,1,1-tris(4-hydroxyphenyl)ethane prepared from the reaction 4-hydroxyacetophenone with phenol. The term "bisphenol tar" as used herein still further includes by-products formed during the condensation reaction between a phenol and an aldehyde, as in the preparation of 1,1-bis(4-hydroxyphenyl) octane from octanal and phenol. The term "bisphenol tar" as used herein still further includes by-products formed during the preparation of bisphenols from phenols and olefins or, in the alternative, phenols and alcohols. Examples of bisphenols prepared from phenol and olefins or alcohols include bisphenol M (4,4'-(1,3-phenylenediisopropylidene) bisphenol), prepared by reaction of phenol with 1,3-bis (isopropenyl)benzene or α,α'-dihydroxy-1,4-diisopropylbenzene in the presence of an acidic catalyst, and dimethylbisphenol M prepared by reaction of o-cresol with 1,3-bis(isopropenyl)benzene or α,α'-dihydroxy-1,4-diisopropylbenzene in the presence of an acidic catalyst. The term bisphenol tar further includes by-products formed in the acid catalyzed transformation of bisphenols, such as BPA, into spirocyclic bisphenols, such as 6,6'-dihydroxyspirobiindane and bicyclic bisphenols, such as cyclic dimer 1.

"BPA tar cracking" as used herein refers to the combined action of heat and catalyst on a BPA tar which results in bond cleavage of BPA tar components susceptible to loss of phenol with formation of olefinic products such as IPP in addition to liberated phenol. In addition, BPA tar cracking includes bond breaking processes of BPA tar components which do not liberate phenol such as the retro ene reaction of IPP linear dimer 1, structure I, to afford two molecules of IPP.

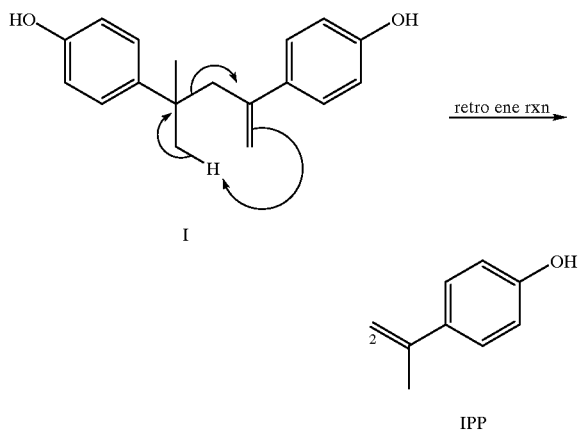

The present invention provides a method for recovering phenol and IPP from BPA tar wherein the BPA tar comprises:
BPA in a range of from about 1 to about 90% by weight,
o,p-BPA in a range of from about 0 to about 90% by weight,
Phenol in a range of from about 0 to about 95% by weight,
IPP linear dimer 1 in a range of from about 0 to about 25% by weight,
IPP linear dimer 2 in a range of from about 0 to about 15% by weight,
IPP cyclic dimer 1 in a range of from about 0 to about 25% by weight,
IPP cyclic dimer 2 in a range of from about 0 to about 15% by weight,
Chroman 1 in a range of from about 0 to about 65% by weight,
Chroman 2 in a range of from about 0 to about 65% by weight,
DMX in a range of from about 0 to about 25% by weight, and
BPX in a range of from about 0 to about 25% by weight.

It is generally preferred that the BPA tar be rich in BPA, o,p-BPA and condensation products of BPA with acetone or IPP such as BPX. Thus the method of the present invention is most advantageously practiced when the BPA tar comprises:
BPA in a range of from about 5 to about 90% by weight,
o,p-BPA in a range of from about 0.1 to about 90% by weight, and
BPX in a range of from about 1 to about 90% by weight.

The BPA tar used as starting material according to the invention may be an amorphous glass or a partially crystalline solid. In either case, the BPA tar is readily converted to a fluid upon heating. The BPA tar may be added to a reaction vessel either as a fluid by mechanical means such as a fluid pump or by gravity flow or transfer effected by pressurization with an inert gas. Alternatively, the BPA tar may be added to the reaction vessel as a solid by means of screw feeders and the like.

The reaction vessel may be a single batch type, heated reactor equipped with a one or more sparge tubes, distillation head, condenser and receiving vessel. BPA tar and catalyst are charged to the reactor. The fluidized BPA tar and catalyst mixture is heated to a temperature in a range from about 180 to about 300° C. while being continuously sparged with an inert gas. Sparging is effected by means of one or more gas inlet tubes inserted into the reactor and extending below the surface of the fluidized tar. An inert gas such as nitrogen or steam or a mixture thereof is introduced at a rate sufficient to thoroughly agitate the fluidized tar. The gas may be preheated or cooled prior to its introduction into the reaction vessel as a means of controlling the temperature of the BPA tar. The volume of gas required depends upon the volume of the reactor being used. The optimum number of sparge tubes, sparge tube diameters and other aspects such as whether or not the sparge tubes are straight, bent or coiled, tipped with metal or ceramic frits and the like is determinable by simple experimentation and may depend upon the size and shape of the reactor, the presence or absence of mechanical agitation in addition to that provided by the sparge and the composition of the BPA tar. The sparging facilitates heat transfer and promotes removal of phenol and IPP from the reaction vessel. The gas introduced through the sparge tubes exits the reactor through the distillation head, condenser and receiving vessel. Phenol and IPP, generated by carbon-carbon bond breaking reactions of BPA tar components, are distilled from the reaction vessel with the aid of the sparge via the distillation head and condenser and are captured in the receiving vessel. As the tar components which can give rise to phenol and IPP are depleted the rate of distillation of phenol and IPP from the tar slows. When distillation of phenol and IPP ceases the "spent" tar residue is removed from the reaction vessel.

Alternatively the reaction vessel may be equipped for continuous BPA tar cracking such that introduction of BPA tar and catalyst, distillation of the phenol-IPP mixture and "spent" tar residue removal are carried out simultaneously. A continuous system of BPA tar cracking may be carried out using a single sparged reaction vessel or a number of sparged reaction vessels in series.

In one of its embodiments the present invention comprises converting the IPP present in the distillate resulting from BPA tar cracking directly to bisphenol A. Since the distillate from BPA tar cracking comprises phenol and IPP the addition of an acidic catalyst to the receiving vessel may be used to promote the known reaction between IPP and phenol to afford bisphenol A. It may be advantageous to charge additional phenol, or additional phenol together with a diluent, to the receiving vessel thereby enhancing the rate of BPA formation and decreasing the formation of unwanted by-products arising from bimolecular reactions of IPP with itself. Various acidic catalysts may be added to the receiving vessel to effect the conversion of the very reactive IPP to the much more stable and easy to handle bisphenol A. These catalysts include sulfonated polystyrenes exemplified by the Amberlyst® acidic resins, Nafion® fluorinated acidic resins, acidic clay catalysts, sulfuric acid, hydrohloric acid, hydrobromic acid and the like. The amount of acidic catalyst added to the receiving vessel is preferably in a range between about 0.001 and about 100 percent by weight based on the weight of the BPA tar charged to the reaction vessel. The amount of phenol added to the receiving vessel is preferably in a range between about 50 and about 1000 percent by weight based on the weight of the BPA tar charged to the reaction vessel. Diluents which may be employed include water, carboxylic acids such as acetic acid, halogenated solvents such as methylene chloride, alcohols such as methanol and ethanol, esters such as ethyl acetate and butyl acetate, acetone and mixtures of acetone and water, hydrocarbons such as heptane, toluene and xylene, and the like. The amount of diluent employed is preferably in a range between about 1 and about 1000 percent based upon the amount of phenol added to the receiving vessel.

The method of the present invention may further comprise mixing the BPA tar with phenol prior to the BPA tar cracking reaction or in the alternative adding phenol to the reaction vessel during the BPA tar cracking reaction. The addition of phenol to the BPA tar enhances the fluidity of the BPA tar, improves heat transfer between the BPA tar and the walls of the reaction vessel. Additionally, the phenol may serve to entrain product IPP in the distillate. The amount of phenol added to the reaction vessel is preferably in a range of from about 10 and about 1000 percent by weight based on the weight of the BPA tar charged to the reaction vessel. In some instances it may be necessary to conduct the BPA tar cracking reaction at slightly elevated pressure in order to achieve a sufficiently high temperature in the reaction vessel to produce an acceptable rate of evolution of BPA tar derived phenol and IPP.

In the absence of a catalyst BPA tar is relatively stable and only slowly evolves phenol and IPP when heated at 180–300° C. The addition of a basic catalyst in an amount ranging from about 10 to about 10,000 parts catalyst per million parts BPA tar accelerates the carbon-carbon bond breaking reactions giving rise to phenol and IPP from components of the tar such as BPA, o,p-BPA, IPP linear dimer 1, IPP linear dimer 2 and BPX. Suitable catalysts include but are not limited to alkali metal hydroxides such as lithium hydroxide, sodium hydroxide and potassium hydroxide; alkaline earth hydroxides such as calcium hydroxide; metal hydrides such as sodium hydride, lithium hydride, calcium hydride and lithium aluminum hydride. Of the basic catalysts listed, sodium hydroxide and potassium hydroxide are preferred. Sodium hydroxide is particularly preferred. The optimum amount of basic catalyst used may depend upon factors such as the composition of the BPA tar. Where higher levels of acidic impurities are present as is sometimes the case there is a need for a correspondingly higher level basic catalyst. Generally however, the inventors have found that a level of basic catalyst in an amount in the range from about 100 to about 5000 parts catalyst per million parts BPA tar is sufficient to achieve a useful rates of phenol and IPP formation from the BPA tar components.

EXAMPLES

The following examples are put forth so as to provide those of ordinary skill in the art with a detailed disclosure and description of how the methods claimed herein evaluated, and are not intended to limit the scope of what the inventors regard as their invention. Unless indicated otherwise, parts are by weight, temperature is in degrees centigrade or is at room temperature and pressure is at or near atmospheric. The materials and testing procedures used for the results shown herein are as follows:

Compositions of starting BPA tar, product phenol and IPP distillate and spent tar residue remaining in the reaction vessel were determined by HPLC calibrated using purified standards for each of the components identified. The HPLC equipment used was a Hewlett Packard model 1090 liquid chromatograph equipped with a 4.6 mm ×100 mm ODS column. Analyses were carried out using acetonitrile:methanol:water as the eluant.

The surprising effect of inert gas sparging was demonstrated on a laboratory scale in a reaction vessel consisting of a glass screw cap culture tube equipped with a cap and Teflon liner. The cap was fitted with an air cooled distillation head and a sparge tube consisting of a 14 gauge stainless steel syringe needle. The distillation head was connected to a vented receiving vial. The sparge tube was connected to a inert gas source and a gas flow meter. The sparge tube could be raised or lowered in the reaction vessel to allow for gas blanketing or sparging, depending on the adjusted height of the syringe needle relative to the fluidized BPA tar (above the fluidized BPA tar for blanketing, below the fluidized BPA tar for sparging). The rate of gas flow was adjusted using a calibrated flow meter. The gas used was "house" nitrogen, and the sparging gas flow rate employed was 35 ml/min. The reaction vessel was heated by immersion in a heated silicone oil bath, controlled by a solid state controller. Temperature was maintained at 250° C. +/−1° C. All experiments involved immersing the culture tube into the bath, which was preset at the cracking temperature.

Examples 1–3

One gram aliquots of BPA tar were cracked with either nitrogen gas blanketing (Example 1) or sparging (Example 2 and 3) at 250° C. in the presence of 1000 ppm NaOH using the laboratory tar cracker described above. In each example the BPA tar was comprised of the following components: o,p-BPA (39.0%), BPA (25.1%), Chroman 1 (12.3%), IPP linear dimers 1 and 2 (6.8%) Chroman 2 (5.7%), DMX (0.7%), IPP (0.4%) and unknown constituents (10%). Values given in parentheses are weight percent. In Example 3 product IPP in the distillate was reacted directly with phenol in the distillate to give BPA. This was effected by collection of the phenol IPP distillate in a stirred, 4 dram vial maintained at 50° C. containing 3.0 grams of phenol and 0.5 grams of Amberlyst 131 (a strongly acidic ion exchange resin, Rohm and Haas Co.). When the IPP was reacted with phenol in this manner the amount of BPA in the product distillate was determined and this value was used to calculate the yield of IPP. For this purpose the yield of phenol with IPP to afford BPA was assumed to be quantitative.

tars generated as by products during the manufacture of 2,2-bis(4-hydroxy-3-methylphenyl)propane; 2,2-bis(3,5-dimethyl-4-hydroxyphenyl)propane; 1,1-bis(4-hydroxyphenyl)cyclohexane; 1,1-bis(4-hydroxyphenyl)-3,3,5-trimethylcyclohexane; 1,1-bis(4-hydroxy-3-

TABLE 1

Distillate analysis of Base Catalyzed BPA Tar Cracking

| Example | Sparged? | Trap?[a] | Weight[b] Distillate | wt[c] PhOH | wt[c] IPP | wt[c] BPA | wt[c] o,p-BPA | wt[c] I & II | wt[c] V & VI | wt[c] VII |
|---|---|---|---|---|---|---|---|---|---|---|
| 1a | No | No | 114 | 84.1 | 12.2 | 0.5 | 1.5 | 0.8 | ND[d] | 0.7 |
| 2a | Yes | No | 779 | 243.8 | 246.2 | 22.6 | 70.1 | 66.2 | 90.4 | 6.2 |
| 3a | Yes | Yes | 710 | NA[e] | 3.0 | 345 | 70.5 | 89.0 | 66.7 | ND[d] |

[a]Phenol/Amberlyst Trap
[b]Weight in milligrams (mg)
[c]Weight in mg of component
[d]Not detected
[e]Value not available

TABLE 2

Effect of Sparging on Spent BPA Tar Residue

| Example[a] | Sparged? | Weight Residue[b] | wt[c] PhOH | wt[c] IPP | wt[c] BPA | wt[c] o,p-BPA | wt[c] I & II | wt[c] V & VI | wt[c] VII | wt[c] VIII |
|---|---|---|---|---|---|---|---|---|---|---|
| 1b | No | 874 | 69.9 | 26.2 | 112.7 | 149.8 | 30.6 | 131.1 | ND[d] | 74.3 |
| 2b | Yes | 208 | 1.9 | 6.2 | 4.0 | 2.9 | 30.3 | 70.1 | Tr[e] | ND[d] |
| 3b | Yes | 206 | NA[f] | 7.0 | 5.4 | ND[d] | 31.3 | 24.7 | Tr[e] | 2.9 |

[a]Residue Examples 1b–3b correspond to distillate Examples 1a–3a in Table 1
[b]Total weight in milligrams of spent tar residue
[c]Weight in mg of component
[d]Not detected
[e]Trace detected
[f]Value not available Table 1 provides data on the distillate generated in Examples 1–3 and Table 2 provides the corresponding data for the residue (spent tar residue) remaining in the reactor after distillation ceased. Comparison of the data for Example 1a and 2a in Table 1 shows clearly the advantageous effect of sparging in terms of phenol and IPP recovery. The more complex mixture obtained in the distillate of Example 2a relative to Example 3a illustrates the advantages of trapping IPP in the distillate with additional phenol and an acidic catalyst complex. Table 2, Examples 1b–3b, is included to provide as complete a mass balance as possible. Here both Examples 2b and 3b illustrate the dramatic reduction of spent tar produced when sparging is used.

The invention has been described in detail with particular reference to preferred embodiments thereof, but it will be understood that variations and modifications can be effected within the spirit and scope of the invention.

What is claimed is:

1. A method of recovering material values from bisphenol tars, said method comprising the following steps:
    a. contacting the bisphenol tar with a basic catalyst in an amount in the range between about 10 and about 10,000 parts catalyst per million parts bisphenol tar,
    b. heating the bisphenol tar catalyst mixture at a temperature in the range between about 180° C. and about 300° C. while sparging the bisphenol tar catalyst mixture with an inert gas, and
    c. collecting the distillate from said bisphenol tar catalyst mixture.

2. A method according to claim 1 wherein the bisphenol tar is selected from among the group consisting of bisphenol methylphenyl)cyclohexane; 1,1,1-tris(4-hydroxyphenyl) ethane; 1,1-bis(4-hydroxyphenyl)octane, and 4,4'-(1,3-phenylenediisopropylidene)bisphenol, 6,6'-dihydroxyspirobiindan and cyclic dimer 1.

3. A method for the recovery of phenol-isopropenylphenol mixtures from BPA tar, said method comprising the following steps:
    a. contacting the BPA tar with a basic catalyst in an amount in the range between about 10 and about 10,000 parts catalyst per million parts BPA tar,
    b. heating the BPA tar catalyst mixture at a temperature in the range between about 180° C. and about 300° C. while sparging the BPA tar catalyst mixture with an inert gas, and
    c. collecting the phenol-isopropenylphenol mixture from said BPA tar catalyst mixture.

4. A method according to claim 3 wherein the BPA tar comprises the following components:

BPA in a range of from about 1 to about 90% by weight,
o,p-BPA in a range of from about 0 to about 90% by weight,
Phenol in a range of from about 0 to about 10% by weight,
IPP linear dimer 1 in a range of from about 0 to about 25% by weight,
IPP linear dimer 2 in a range of from about 0 to about 15% by weight,
IPP cyclic dimer 1 in a range of from about 0 to about 25% by weight,
IPP cyclic dimer 2 in a range of from about 0 to about 15% by weight, Chroman 1 in a range of from about 0 to about 65% by weight, Chroman 2 in a range of from about 0 to about 6 5% by weight, DMX in a range of from about 0 to about 25% by weight, and BPX in a range of from about 0 to about 25% by weight.

5. A method according to claim 3 wherein the BPA tar comprises the following components:

BPA in a range of from about 5 to about 90% by weight, o,p-BPA in a range of from about 0.1 to about 90% by weight, and BPX in a range of from about 1 to about 90% by weight.

6. A method according to claim 3 wherein the BPA tar is contacted with a basic catalyst in a reaction vessel equipped with one or more sparge tubes.

7. A method according to claim 3 wherein the inert gas of step (b) is selected from the group comprising nitrogen, argon and steam.

8. A method according to claim 3 wherein the basic catalyst is selected from among the group comprising lithium hydroxide, sodium hydroxide or calcium hydroxide.

9. A method according to claim 3 wherein the amount of basic catalyst is in the range from about 100 to about 2000 parts catalyst per million parts BPA tar.

10. A method for recovering phenol and bisphenol A values from a BPA tar, said method comprising the following steps:

a. contacting the BPA tar with a basic catalyst in an amount in a range between about 10 and about 10,000 parts catalyst per million parts BPA tar, b. heating the BPA tar catalyst mixture at a temperature in the range between about 180° C. and about 300° C. while sparging the BPA tar catalyst mixture with an inert gas, and c. collecting the phenol-isopropenylphenol mixture from said BPA tar catalyst mixture into a receiving vessel maintained at a temperature in a range from about 0 to about 100° C. containing a mixture comprising phenol and an acidic catalyst.

11. A method according to claim 10 wherein the receiving vessel is maintained at a temperature in a range between about 40° C. and about 60° C.

12. A method according to claim 10 wherein the acidic catalyst of step (c) is a sulfonated polystyrene resin.

13. A method according to claim 10 in which the mixture comprising phenol and an acidic catalyst of step (c) further comprises a diluent.

14. A method according to claim 13 wherein the amount of phenol used in step (c) is in a range from about 50 to about 500 percent of the based on the weight of the BPA tar employed.

15. A method according to claim 14 wherein the diluent of step (c) is water.

16. A method for recovering phenol and isopropenylphenol from a BPA tar comprising BPA and o,p-BPA, the total amount of BPA and o,p-BPA being in a range from about 10 to about 90 weight percent of the BPA tar, said method comprising the following steps:

a. contacting the BPA tar with a basic catalyst in an amount in a range between about 100 and about 5,000 parts catalyst per million parts BPA tar, b. heating the BPA tar catalyst mixture at a temperature in the range between about 220° C. and about 280° C. while sparging the BPA tar catalyst mixture with an inert gas, and c. collecting the phenol-isopropenylphenol mixture from said BPA tar catalyst mixture.

17. A method according to claim 16 in which the basic catalyst of step (b) is selected from the group consisting of sodium hydroxide and potassium hydroxide.

18. A method according to claim 16 in which the BPA tar-basic catalyst mixture is heated to a temperature in a range between about 245° C. and about 255° C.

19. A method according to claim 16 in which the phenol-isopropenylphenol mixture of step (c) is further reacted with a mixture comprising a sulfonated polystyrene acidic catalyst together with an amount of phenol equal to about 3 to about 5 times the weight of said BPA tar.

20. A method according to claim 19 in which the weight of sulfonated polystyrene catalyst is at least about 0.001% of the weight of said phenol.

21. A method according to claim 19 in which the phenol-isopropenylphenol mixture of step (c) is further reacted at a temperature in a range between about 40° C. and about 60° C.

22. A method according to claim 16 in which the BPA tar contains an amount of BPA in the range of from about 60 to about 70 weight percent.

23. A method according to claim 16 in which the BPA tar contains an amount of BPA in the range of from about 10 to about 30 weight percent.

24. A method according to claim 16 in which the BPA tar contains an amount of BPA in the range of from about 1 to about 10 weight percent.

* * * * *